United States Patent [19]
Enzler et al.

[11] Patent Number: 5,541,855
[45] Date of Patent: Jul. 30, 1996

[54] DEVICE FOR TESTING UNSET CONCRETE AND MORTAR

[75] Inventors: Ruedi Enzler, Lichtensteig, Switzerland; Elfrun Lembke, Jena, Germany; Gunter Lueth, Jena, Germany; Peter Zimmerman, Jena, Germany; Eberhard Schmidt, Jena, Germany

[73] Assignees: Atrof Bauphysik AG, Zug, Switzerland; Jenoptik GmbH, Jena, Germany

[21] Appl. No.: 375,006

[22] Filed: Jan. 18, 1995

Related U.S. Application Data

[63] Continuation of Ser. No. 39,461, Apr. 23, 1993, abandoned, which is a continuation of PCT/CH92/00174, Aug. 28, 1992.

[30] Foreign Application Priority Data

Aug. 28, 1991 [CH] Switzerland ................. 2526/91

[51] Int. Cl.$^6$ ............................................. B01F 15/00
[52] U.S. Cl. ................... 364/552; 73/803; 366/142
[58] Field of Search ................... 73/73, 54.13, 803; 364/502, 505, 506, 507, 508, 552, 424.02, 478, 479, 579, 580; 366/140, 142

[56] References Cited

U.S. PATENT DOCUMENTS

| | | | |
|---|---|---|---|
| 3,595,072 | 7/1971 | Richards | 73/803 |
| 3,609,316 | 9/1971 | Brosset | 364/479 |
| 4,065,959 | 1/1978 | Richardson | 73/54.13 |
| 4,186,592 | 2/1980 | Eirich et al. | 73/73 |
| 4,318,177 | 3/1982 | Rapp et al. | 364/502 |
| 4,484,468 | 11/1984 | Gau et al. | 364/509 X |
| 4,538,467 | 9/1985 | Stoll | 73/803 |
| 4,582,139 | 4/1986 | Childs et al. | 166/293 |
| 4,615,215 | 10/1986 | Sugimoto et al. | 364/552 |
| 5,041,987 | 8/1991 | Kuwahara et al. | 364/505 |
| 5,098,847 | 3/1992 | Welker | 436/180 |
| 5,239,249 | 8/1993 | Ono | 364/424.02 |

FOREIGN PATENT DOCUMENTS

| | | |
|---|---|---|
| 0125774 | 11/1984 | European Pat. Off. |
| 2092308 | 8/1992 | United Kingdom |

*Primary Examiner*—Edward R. Cosimano
*Attorney, Agent, or Firm*—McAulay, Fisher, Nissen, Goldberg & Kiel

[57] ABSTRACT

A rotating testing device can be connected to a base unit. A temperature sensor can also be connected to the base unit. The testing device has probe heads. The probe heads are immersed and rotated in the liquid concrete and the force required for rotation is measured in the base unit. Various concrete recipes are stored in a memory of the base unit. Data concerning the concrete are calculated by comparison with the force required to rotate the testing device with the force derived from a respective stored characteristic line and are read from a display field. A concrete recipe and specific measurements are selected by actuating keys which select the respective electronic processes in the base unit for measurement and comparison with stored characteristic data.

45 Claims, 5 Drawing Sheets

5,541,855

DEVICE FOR TESTING UNSET CONCRETE AND MORTAR

This is a continuation of application Ser. No. 08/039,461, filed Apr. 23, 1993 now abandoned, which is a continuation of PCT/CH92/00174, filed Aug. 28, 1992.

BACKGROUND OF THE INVENTION

1. Field of the Invention

The present invention concerns a device for testing fresh or unset concrete and mortar.

2. Background Art

To carry out such testing of unset concrete and mortar, samples are taken at the construction site and tested in a laboratory far from the site. Since construction proceeds during this testing, the results of the tests are often available only after the construction has already progressed much further so that defects are only discovered after it is practically no longer possible to remedy them, e.g. when parts of the erected building would have to be demolished. This is a very unsatisfactory situation.

In addition, a large part of the damage occurring in concrete constructions can be traced back to errors in the processing of the concrete. Accordingly, it is necessary to test the products produced by companies at the points of delivery, that is, in the case of concrete, prior to pouring. For example, tests should be carried out when delivery of the fresh concrete on the construction site is made by the ready-mixed concrete factory to the firm executing the construction work. Testing of unset concrete, as well as hardened concrete and starting materials is determined by the Swiss Engineer and Architect, or SIA, Standard 162, edition 1989. In order to carry out these tests, particularly on unset concrete, it has substantially been the case that a large number of very different devices are necessary. Acquiring and storing the many different devices obtained from various producers is extremely costly.

OBJECT AND SUMMARY OF THE INVENTION

A primary object of the present invention is to overcome the above disadvantages.

The device, according to the invention, comprises a base unit and a number of selectably attachable testing devices for generating measurement data, at least one of the testing devices is constructed so as to be rotatable. The base unit has at least one connection for a testing device, an energy source for operating the device independently of a main electrical supply, a computing unit, a selector device for selecting the test to be carried out and thereby the computing processes to be carried out by the computing unit based on the measurement data generated by the testing devices, a display, and a converter for converting the output data from the computing unit into test results which can be read at least by the display.

In the following, the subject matter of the invention is explained in more detail by way of example with reference to the drawing and the scope of the invention will be pointed out in the appended claims.

DESCRIPTION OF THE PREFERRED EMBODIMENT

The tests prescribed in compliance with the SIA Standard (1968) are listed in the table below.

Figures 1, 2, 3:
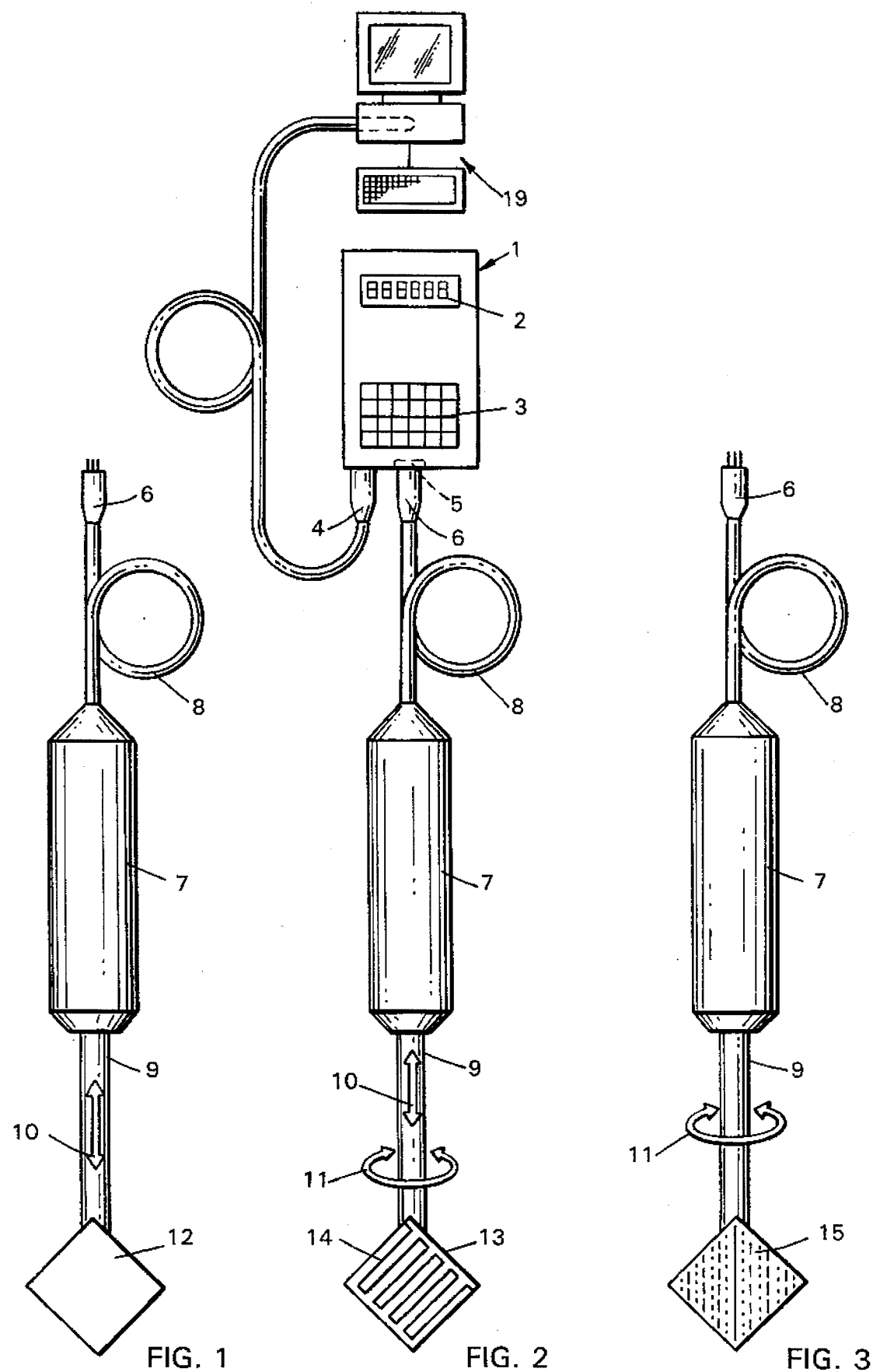
FIG. 1 shows a first construction of a testing device.
FIG. 2 shows a second construction of a testing device which is connected with the base device which can be connected in turn with an electronic data processing system.
FIG. 3 shows another construction of a testing device.

The first construction of the device according to the invention shown in FIGS. 1–3 substantially includes a portable base unit 1. The dimensions of this base unit 1 roughly correspond to those of a pocket calculator. The base unit 1 contains an energy source in the form of one or more batteries, a display 2, a computing unit which will be discussed at greater length in the following, and a keyboard 3.

A first storage or memory in which the determined measurement data can be stored is also installed in the base device 1. Standardized concrete recipes are stored in an additional memory unit in the form of characteristic lines. In particular, characteristic lines are stored for a predetermined particle-size distribution or grading curve, origin of aggregates, additives (frost protection, super-liquefiers, air-entraining agents, etc.). These characteristic lines are stored so as to take into account the standards of different countries in which the device is used. The base unit 1 can be connected, via a connection 4, with an electronic data processing system 19 which can be used e.g. for archive filing, statistics, etc. As will be shown, the base unit 1 with the testing devices is always only used at the construction site. The determined measurement data can be stored in the base unit 1 and, after work is completed, the base unit is brought e.g. to the office of the construction engineer and there connected to the electronic data processing system for the aforementioned purposes.

The base unit can be connected with different testing devices which serve to carry out the respective test and can contain different probe heads. To this end, the base unit 1 has an input connection 5 and the various testing devices have e.g. plug-type connections which can be connected with, i.e. plugged into, the input connection 5 when carrying out the test in question.

Each testing device has a handle 7, see FIGS. 1–3, and the respective plug-type connection 6 is connected with the handle 7 via a cable 8. An electronic circuit or a control corresponding to the respective task is arranged in the respective handle 7. The shape of the handles 7 shown in FIGS. 1–3 is not compulsory; they can also be round, square, long or short depending on the task. The handle is further connected with a measuring probe head via a long connection member 9. The connection member 9 can be rigid or flexible, constructed as a tube or hose line, and can also contain electric lines which is compatible from the respective probe head to the electronic circuit in the base unit 1 or can be correspondingly processed and displayed.

In the event that the connection member is rigid, a drive can be present in the handle, depending on the respective task, which, as shown by the double arrow 10 in FIG. 1, can effect a vibrating reciprocating movement of the probe head. The drive can be of such a kind as to cause a rotating movement of the probe head, as indicated by reference number 11, in addition to the vibrating movement according to the double arrow 10 in FIG. 2. Obviously, it is also possible to construct the drive in such a way that it can produce only a rotating movement of the probe head according to reference number 11, as is shown in FIG. 3.

Further, the connection members 9 can take the form of a tube or hose so that water under pressure, compressed air or a vacuum (suction pull) can be transmitted to the probe heads so as to be controlled by the handle 7.

The probe heads can assume different shapes depending on the task at hand. The probe head 12 shown in FIG. 1 is in the shape of a plate which is square as seen from the top. For example, a temperature sensor may be arranged in this probe head 12 so that the construction according to FIG. 1 can be used as a temperature probe (vibration is not strictly necessary in this case).

Figure 4:
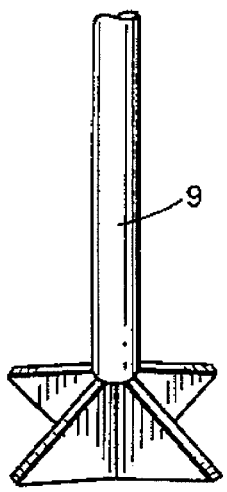
FIG. 4 shows a top view of a star-shaped probe head.
Figure 5:
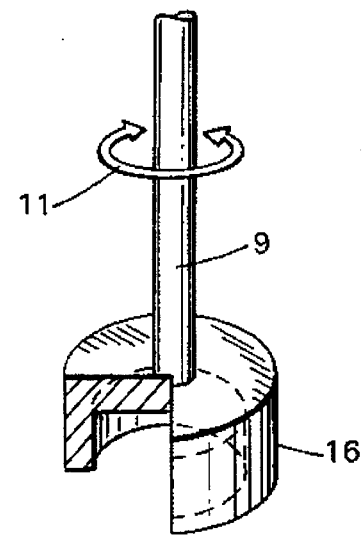
FIGS. 5 and 6 show probe heads of testing devices constructed as rotating bodies.
Figure 6:
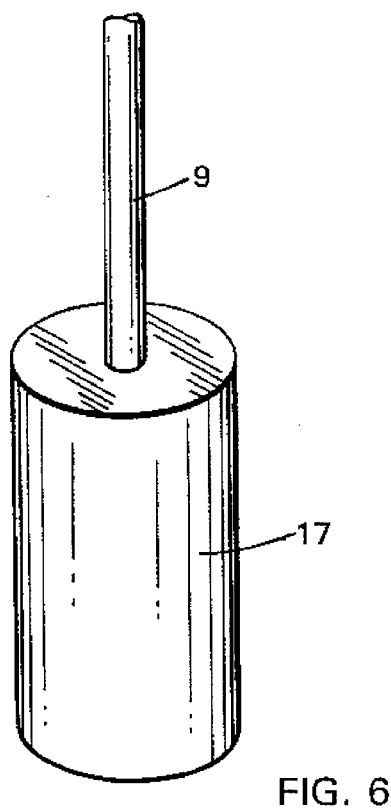
Figure 7:
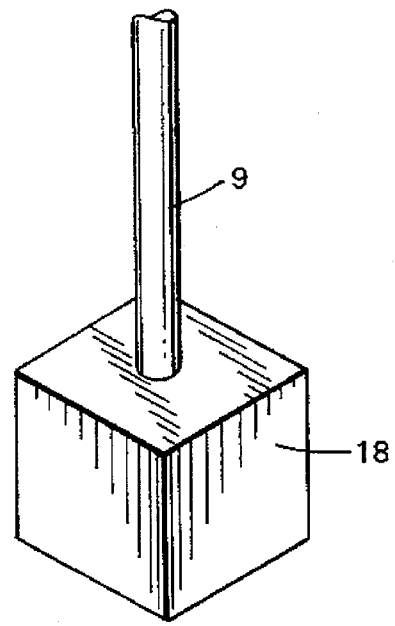
FIG. 7 shows a cube-shaped probe head of a testing device.

The probe head 13 according to FIG. 2 is also shaped like a square plate as seen from the top, a conductor 14 being inserted in same. This probe can be used e.g. as a water-cement ratio probe (again not necessarily movable). The probe head according to FIG. 3 which is furnished with perforations 15 can be used as a consistency probe and, as shown in FIG. 4, can be star-shaped as seen from the top. An annular probe head 16 is shown in FIG. 5. The latter can also be rotated e.g. to produce abrasion, and the abraded material can be sucked into the handle 7 through the tubular connection member 9 for analysis. A cylindrical probe head 17 is shown in FIG. 6. FIG. 7 shows a cube-shaped probe head 18. Although the connection member 9 projects from one side of the cube 18 in this instance, the connection member 9 can also be attached so as to be aligned with a spatial diagonal of the cube 18.

The dimensions of the probe heads can range from several centimeters to a decimeter as seen along the lateral lengths depending on the task to be performed and in the same existing probe devices.

Depending on the test to be carried out, e.g. SIA 162 (1968), a probe head is selected and connected with the base unit 1 via the plug-type connection 6. The computing processes to be carried out in the computing unit are then selected by means of the keyboard 3 to obtain a digital display in the field 2. This display can be further supplemented by a displayed identification of the respective test so that when carrying out the water-cement ratio test, as shown in FIG. 2, not only is there a corresponding digital display, but identifying letters, i.e. W/C, in the present example, are also displayed. Additional keys serve to start and stop measurement, to store the measured values and, of course, to transmit same to the electronic data processing system.

The computing unit in the base unit 1 is further constructed in such a way that it calculates an additional value corresponding to a test to be carried out from a plurality of measured values and can display it.

Examples of the measurements and tests which can be carried out by the device according to the invention are listed in the following. The numbering corresponds to the test numbers of the SIA table mentioned above:

Nos. 1/2 cylinder pressure vessel

No. 3 electronically calculated modulus of elasticity of 1/2 and 4

No. 4 laser deformation measurement based on holographic interferometry

No. 5 calculated water conducting property from 1/2, 3, 4

No. 7 calculated water conducting property from 1/2, 3, 4, 5

No. 8 cavity measurement through temperature change vessel and calculated values from No. 5

No. 9 cavity measurement through temperature change vessel and calculated values from No. 5

No. 10 rotation vessel with abrasion probe surfaces

No. 12 chemical addition probe with integrated chemicals vessel

No. 13 electronically calculated value from 1/2, 3,

No. 16 same as No. 12

No. 17 same as No. 12

No. 18 calculated values from Nos. 19+20

No. 19 moisture probe in relation to the predetermined cement proportioning and No. 20

No. 20 rotation probe with surface profile (star, cylinder, corrugated) depending on maximum concrete grain diameter (stones)

To carry out the cube or drill-core compressive strength tests, i.e. test No. 1 or 2, a cylinder pressure vessel is used as probe head, e.g. according to FIG. 6. It should be noted that the walls of the cylinder pressure vessel can also be constructed so as to be flexible and not rigid. The creep and shrinkage values, test No. 4, is carried out by means of a laser deformation measurement based on holographic interferometry. After tests Nos. 1, 2 and 4 have been carried out and their results stored in the base unit 1, the modulus of elasticity can be calculated from these three tests electronically in the base unit 1 by simply pressing the corresponding key.

SIA test No. 5, water conducting property, is calculated from the values of tests Nos. 1/2, 3 and 4. The porosity, No. 7, is calculated from the data of tests Nos. 1/2, 3 and 5. Test No. 8, frost alternation behavior, is given by cavity measurement by means of a temperature change vessel, the value of the frost alternating behavior being given by this measurement and the calculated values from test No. 5. Frost-thaw salt behavior, test No. 9, is given by a cavity measurement by means of a temperature change vessel and by the calculated values according to test No. 5.

The abrasion behavior test, No. 10, is carried out with a rotation vessel with abrasion probe surfaces, i.e. a probe head constructed roughly in accordance with the probe head 16 according to FIG. 5. The cleanliness test, No. 12, is carried out with a chemical addition probe with integrated chemicals vessel, roughly in the form of probe head 17 according to FIG. 6 or also probe head 18 according to FIG. 7. The powder grain content, test No. 13, is given by the electronically calculated value from tests Nos. 1/2, 3, 10 and 18 (see below). The mixing water test, No. 16, and the suitability test (reagents and additives), test 17, are carried out with a chemical addition probe as in test No. 12. The yield, test No. 18, is given by a calculated value from tests Nos. 19 and 20.

The water content and water-cement ratio, test No. 19, is calculated with a moisture probe (see also FIG. 2) in relation to the predetermined cement proportioning and from the values according to test No. 2.

Depending on the maximum cement grain diameter (stones), the consistency test, test No. 20, is carried out by a rotating probe with a surface profile of the probe head, e.g. FIG. 5 or 6, which can be cylindrical, corrugated or also constructed in a star-shaped manner as seen from the top in FIG. 4.

Thus, it can be seen that the test to be carried out determines the choice of probe or probe head constructed for this purpose. The corresponding testing device is connected to the base unit and the display 2 is then activated via the computing unit in the base unit by pressing the corresponding key 3. If a plurality of determined values are to be displayed, the corresponding tests are carried out beforehand again by means of the corresponding testing devices and the values are stored in the memory of the base unit 1. A computing process based on these stored values is then carried out by pressing the appropriate key, and the results are then displayed again in the display 2.

Figure 8:
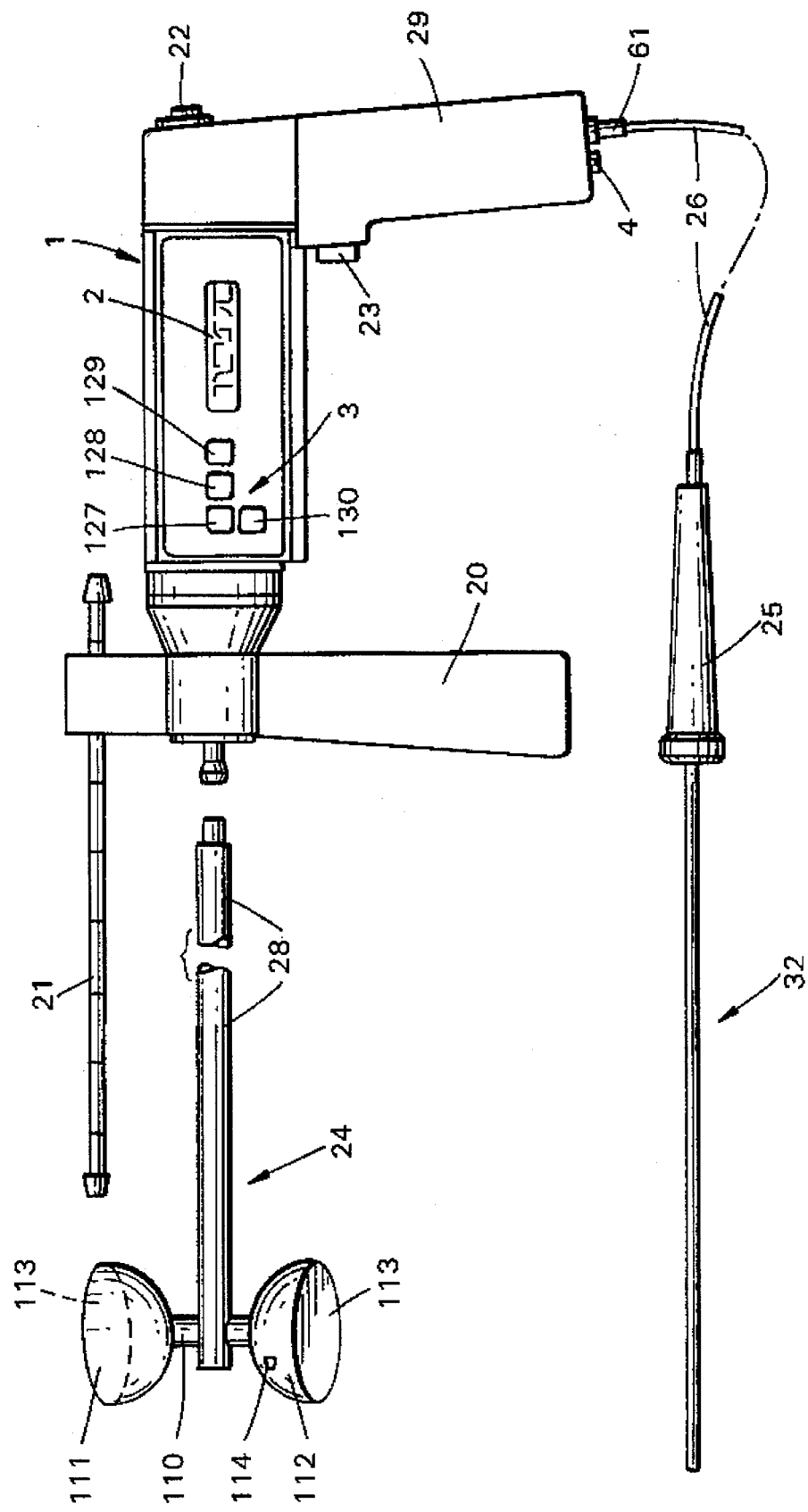
FIG. 8 shows a simplified side view of another construction of the device according to the invention with another construction of a testing device and probe head.
Figures 9, 10:
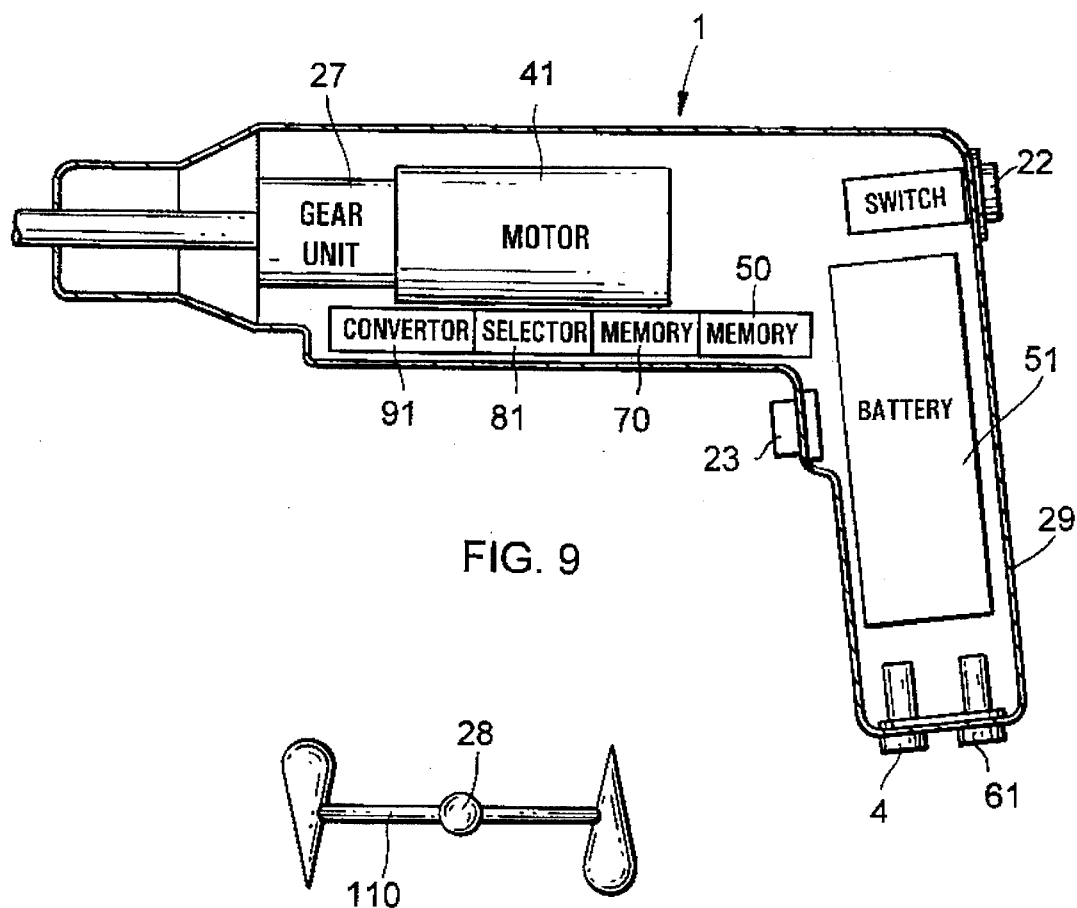
FIG. 9 is a schematic view of a section through the base unit shown in FIG. 8.
FIG. 10 is a plan view of another variant of probe heads.
Figure 11:
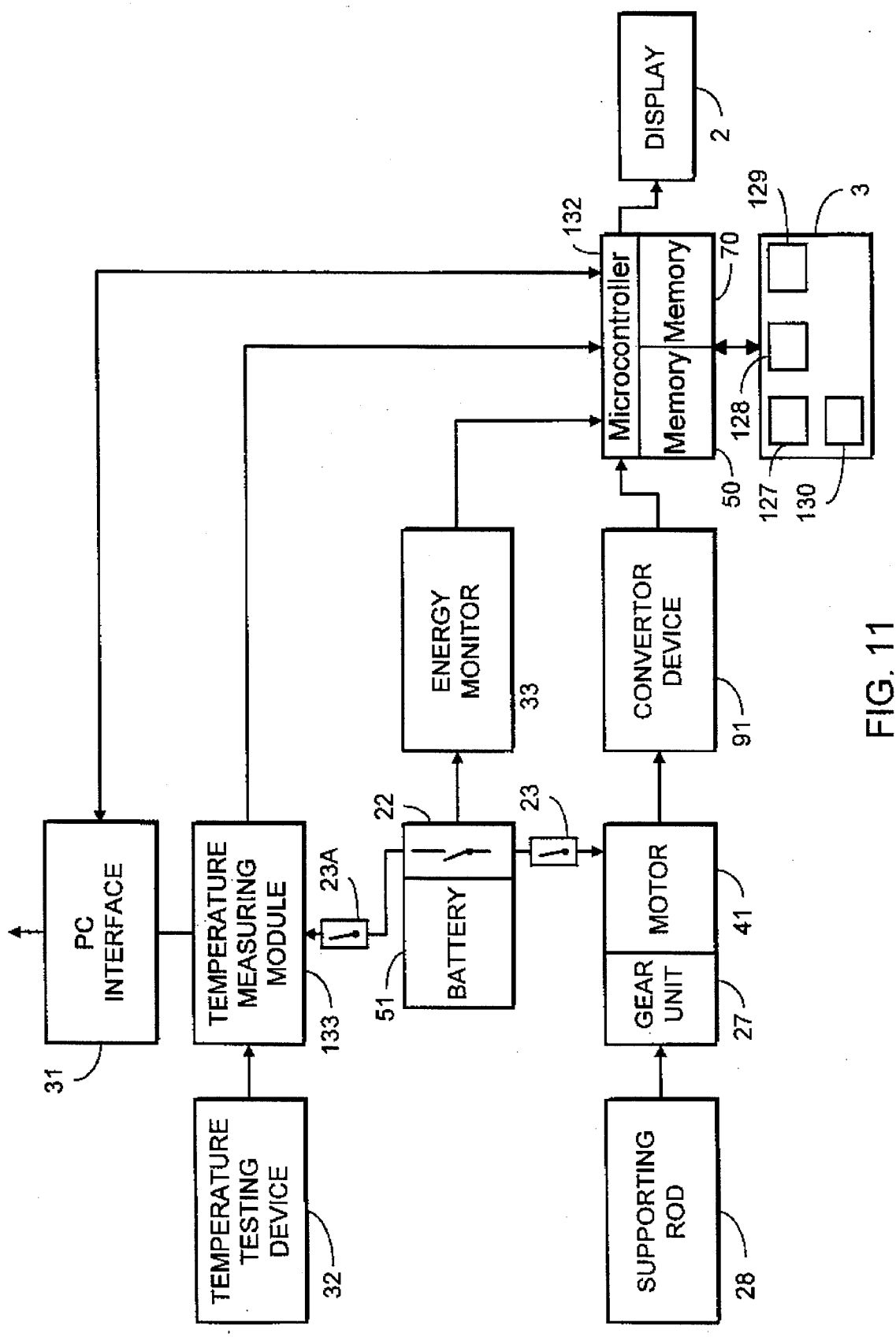
FIG. 11 shows a schematic wiring diagram of the device of FIG. 8.

Another construction of the device according to the invention is shown in FIGS. 8 and 9. The block wiring diagram pertaining to this construction is shown in FIG. 11. It should be noted that the basic construction of this block wiring diagram is identical to the circuit of the first construction of the device, according to the invention, which was discussed previously.

This further construction again contains the base unit 1 in which a motor 41 and a gear unit 27 are arranged. In addition, the base unit 1 contains electronic circuits, namely a memory unit 70 for characteristic lines, a selector device 81, a converter device 91 and a memory 50 for the measurement data. The function of these electronic circuits (which apply to both constructions) is discussed in the following. A rechargeable storage battery 51 is arranged in the pistol grip 29. A charging device can be connected to the latter via a plug-in connection 61. Due to the storage battery 51, the device can be used without a mains. This means that there is no need for a connection to an electrical mains at the respective testing site in order to carry out the different tests.

The base unit 1 has another handle 20. To ensure that any series of measurements is always carried out at the same depth in the unset concrete, a measuring rod 21 is inserted in the handle 20 so as to be longitudinally displaceable in the latter so that the respective immersion depth of the measuring probes or probe heads can be exactly measured.

Further, the base unit 1 has an on/off switch 22. The current supply to the various electrical and electronic units in the base unit is switched on and off substantially by means of this switch 22.

The individual measurements are initiated (when the switch 22 is turned on) by the switch 23. As can be seen from the drawing, the two switches 22, 23 are press-button switches. With reference to FIG. 11, a monitoring unit 33, including overload protection, is arranged in the circuit immediately subsequent to the switch 22. The micro-controller 132 with memories 50 and 70 is arranged subsequent to the latter. The electrical energy which proceeds from the storage battery 51 by switching on the switch 22 is monitored by the unit 33 to prevent damage to the circuit. In addition to the plug-in connection 61, there is an additional connection 4 serving to connect the device with an electronic data processing system (see FIG. 2). In doing so, measurement data stored in the memory 50 can be transmitted to an electronic computer for further evaluation. The PC interface of this electronic computer is designated by 31 in FIG. 11.

Different testing devices can be connected to the base unit 1. A first testing device, e.g. testing device 24, is the so-called consistency probe. The testing device has a supporting rod 28 which can be connected with the gear unit 27 via a screw connection and rotated correspondingly by means of the motor 41. The supporting rod 28 has a cross-piece 110 at its far end. This cross-piece 110 carries two semispherical probe heads 111 and 112. The planar surface portion of the semisphere of the probe head 111 is designated by 113. Additional measurement probes can be inserted in one or both of these probe heads 111, 112. For example, the location for insertion of a moisture probe in the probe head is indicated at reference number 114. When the switch 22 is switched on and switch 23 is then pressed, the testing device 24 can be rotated for carrying out the tests.

A temperature testing device with handle 25 is designated by reference number 32. The temperature testing device 32 can be connected to the plug-in connection 61 via a cable 26. The plug-in connection 61 thus serves for connecting to a charging device for the storage battery on the one hand and as a connection for the temperature sensor, i.e. testing device 32, on the other hand.

The display 2 is arranged at the side of the base unit 1 and displays various data which will be discussed in the following. Further, a foil keyboard is arranged at the base unit 1. The key 127 is the temperature selecting key, i.e. when this key 127 is pressed a measurement of the temperature is carried out in the base unit 1 when the temperature testing device 32 is connected, the temperature being indicated in the field of the display 2.

Key 128 is used to select different measurement data which are determined when the measurement probe 28 rotates. The key 128 must be pressed successively to select a measurement to be carried out. Key 129 is used to select one of the characteristic lines stored in the memory unit 70 for the unset concrete recipe to be examined and, finally, key 130 serves to calibrate the device.

The rotating testing device 28 is basically a consistency probe. It is driven by the motor 41 at a speed of approximately 5–20 r.p.m. via the gear unit 27.

The cross-piece 110 with the two probe heads 111 and 112 securely connected with it is connected with the supporting rod 11 so as to be rotatable around its longitudinal axis. The angular position of the semispherical probe heads 111, 112 can accordingly be freely selected corresponding to the consistency of the substance in which it is immersed. For example, it is possible to select an optional oblique position of the planar surface portions 113 relative to the supporting rod 28. A change of 180° in the rotating position of the probe heads 111, 112 around the cross-piece 110 is also possible. In the case of concrete, the probe heads 111, 112 can be positioned e.g. so as to lead with the respective curved surface portion of the semispherical probe heads 111, 112. In the case of mortar, which is rather liquid, it is preferable that the planar surface portion 113 of the semispherical probe heads 111, 112 be in the lead.

As is shown in the top view according to FIG. 10, other constructions of the probe heads can also be used. For example, tear-shaped probe heads according to the construction shown in FIG. 10 can also be used.

The testing device rotates when operated. In so doing, a torque can be determined as a function of the force to be exerted (measured by the output of the motor) and as a function of the lever arm of the probe via in the converter device 91 (see FIG. 11), whose output is fed, via the microcontroller 132, to the display field 2 in which the scalar value (so-called FCT value) is displayed.

Standardized concrete recipes are stored in the memory unit 70 in the form of characteristic lines. Characteristic lines are stored in particular for a predetermined particle-size distribution or grading curve, origin of aggregates, additives (frost protection, super-liquefiers, air-entraining agents, etc.). The standards for different countries are also taken into account in corresponding characteristic lines.

The measurement process is effected in the following manner. First, the desired immersion depth of the probe heads 111, 112 is determined by means of the measurement rod 21 and then the device is switched on by pressing the on/off switch 22. Key 23 is then pressed. The supporting rod 28 with the probe heads 111, 112 rotates in the air and the internal calibration of the device is effected. This process lasts approximately 4 seconds and is terminated automatically. The measurement probes 111, 112 are then inserted e.g. into the unset concrete until the measuring rod 21 contacts the surface of the concrete. By pressing the switch 23, the testing device is started, the force required for rotation is measured by known processes and indicated in the display field 2 as so-called FCT data via the converter device 91 and the microcontroller 132. The rotating period is also ended automatically in this case. Accordingly, the same measurement and the same process can be carried out in different places in the concrete to be tested. The different measurements result in a mean value which is stored in the memory 50. The testing device 24 is lifted out of the concrete.

The following procedure is followed for reading out the measured values. By pressing key 129, the memory unit 50 is controlled in such a way that data such as grading curve, largest grain, and number of stored characteristic line for a predetermined concrete recipe appear in the display field 2. In order to display these data for the concrete to be measured it is necessary to press the key 129 again.

By pressing the key 128 once, the slump A of the concrete can be displayed based on the value determined by the operation of the device 24. The displayed value is based on the characteristic line stored in the memory unit 70 and retrieved by the measurement key 128 and the selector device 81.

When key 128 is pressed again, the water-cement ratio is retrieved and shown in the display 2. The displayed water-cement ratio is based on the characteristic line stored in the memory unit 70 and selected by the selector device 81. By pressing key 128 a third time, the compressive strength D after 28 days can be displayed.

These three measurement data can be read out and evaluated immediately. It is also possible to store the displayed values in the memory 50 by subsequently actuating the calibrating key 130. These measurement data stored in the memory 50 can then be played over on a PC, e.g. in a laboratory.

Testing device 32 serves to measure temperature. It is connected with the base unit 1 via the plug-in connection 61. The device is started by switching on switch 22. Key 127 is then pressed so that the temperature measured by the temperature sensor is displayed in the display field 2 and a mean value of a plurality of values can be indicated.

The output of the testing device 32 is fed to a temperature measuring module 133 in which the measured value supplied by the testing device 32 is converted into a signal for transmission to the microcontroller 132, from which the signal necessary for the display field 2 is finally supplied. The instantaneous value of the temperature can be displayed by pressing switch 23 again, wherein the switch 23A in FIG. 10 is closed.

In this way, unset concrete, mortar and similar cement-related substances can be tested in situ by a simple device, e.g. according to the constructions of the inventive device which are shown in the drawings, and any defects can be detected immediately.

While the foregoing description and drawings represent the preferred embodiments of the present invention, it will be obvious to those skilled in the art that various changes and modifications may be made therein without departing from the true spirit and scope of the present invention.

What is claimed is:

1. A portable, hand-held device for on-site testing of unset concrete and mortar, comprising:

a base unit and a plurality of selectably attachable testing devices for generating measurement data of different parameters, at least one of said devices being constructed so as to be rotatable, said base unit having at least one connection for a testing device, an energy source for operating the device independently of a main electrical supply, a computing unit, selector means for selecting a test to be carried out and thereby computing processes to be carried out by said computing unit based on measurement data generated by said testing devices, and a display for reading and displaying output data received from said computing unit.

2. A device according to claim 1, wherein the base unit has a memory for storing the measurement data and a connection for the transmission of the stored measurement data to an electronic data processing system.

3. A device according to claim 1, wherein the base unit has a memory unit for storing standardized concrete recipes which can be retrieved by the selector means and fed to the display means.

4. A device according to claim 1, wherein a stationary testing device is included which is outfitted with a temperature sensor.

5. A device according to claim 1, wherein at least a number of testing devices have a probe head in which an additional measurement probe is installed.

6. A device according to claim 1, wherein a testing device has a plate-shaped probe head which is square as seen from the top.

7. A device according to claim 1, wherein a testing device has a cube-shaped probe head.

8. A device according to claim 1, wherein a testing device has a star-shaped probe head.

9. A device according to claim 1, wherein a testing device has an annular or cylindrical probe head.

10. A device according to claim 1, wherein at least one rotatable testing device has a probe head and a rigid, long connection member, and wherein a drive is included, having a motor, which is arranged in the base unit, and wherein the rigid connection piece is constructed for a detachable connection with the drive.

11. A device according to claim 10, wherein the rotatable testing device has a supporting rod which can be connected to the drive and has two probe heads at its end which are supported by a cross-piece so as to be arranged diametrically opposite one another.

12. A device according to claim 1, wherein at least one testing device has a probe head and a handle portion, at least one electronic circuit or control being installed in the handle portion for converting measured values occurring during operation of the probe head for transmission to the computing unit, which probe head is connected with the handle portion via a long, rigid or flexible connection member.

13. A device according to claim 12, in which the probe head is connected with the handle portion via a rigid connection member, wherein the connection member is connected with a drive which is arranged in the handle portion and serves to generate a rotating movement and/or a vibrating reciprocating movement of the connection member.

14. A device according to claim 13, wherein the connection member is constructed as a tube for the transmission of water under pressure, compressed air or a vacuum.

15. A portable, hand-held device for on-site testing of unset concrete and mortar, comprising:

a base unit and a plurality of selectably attachable testing devices for generating measurement data of different parameters, at least one of said devices being constructed so as to be rotatable, said base unit having at least one connection for a testing device, an energy source for operating the device independently of a main electrical supply, a computing unit, selector means tier selecting a test to be carried out and thereby computing processes to be carried out by said computing unit based on measurement data generated by said testing devices, said computing processes including selective determination of at least one of a) water/cement ratio and c) compressive strength from a test of said rotatable device, and a display for reading and displaying output data received from said computing unit.

16. A device according to claim 15, wherein the base unit has a memory for storing the measurement data and a connection for the transmission of the stored measurement data to an electronic data processing system.

17. A device according to claim 15, wherein the base unit has a memory unit for storing standardized concrete recipes which can be retrieved by the selector means and fed to the display.

18. A device according to claim 15, wherein a stationary testing device is included which is outfitted with a temperature sensor.

19. A device according to claim 15, wherein at least a number of testing devices have a probe head in which an additional measurement probe is installed.

20. A device according to claim 15, wherein a testing device has a plate-shaped probe head which is square as seen from the top.

21. A device according to claim 15, wherein a testing device has a cube-shaped probe head.

22. A device according to claim 15, wherein a testing device has a star-shaped probe head.

23. A device according to claim 15, wherein a testing device has an annular or cylindrical probe head.

24. A device according to claim 15, wherein at least one rotatable testing device has a probe head and a rigid, long connection member, and wherein a drive is included, having a motor, which is arranged in the base unit, and wherein the rigid connection piece is constructed for a detachable connection with the drive.

25. A device according to claim 24, wherein the rotatable testing device has a supporting rod which can be connected to the drive and has two probe heads at its end which are supported by a cross-piece so as to be arranged diametrically opposite one another.

26. A device according to claim 15, wherein at least one testing device has a probe head and a handle portion, at least one electronic circuit or control being installed in the handle portion for converting measured values occurring during operation of the probe head for transmission to the computing unit, which probe head is connected with the handle portion via a long, rigid or flexible connection member.

27. A device according to claim 26, in which the probe head is connected with the handle portion via a rigid connection member, wherein the connection member is connected with a drive which is arranged in the handle portion and serves to generate a rotating movement and/or a vibrating reciprocating movement of the connection member.

28. A device according to claim 27, wherein the connection member is constructed as a tube for the transmission of water under pressure, compressed air or a vacuum.

29. A portable, hand-held device for on-site testing of unset concrete and mortar, comprising:

a base unit and a plurality of selectably attachable testing devices for generating measurement data of different parameters, at least one of said devices being constructed so as to be rotatable, said base unit having at least one connection for a testing device, an energy source for operating the device independently of a main electrical supply, memory means for providing a store of characteristic lines representing standardized concrete recipes, a computing unit, selector means for selecting a test to be carried out and thereby computing processes to be carried out by said computing unit based on measurement data generated by said testing devices, said selector means for selecting a signal of a characteristic line from said memory means for processing measurement data of said rotatable device, and a display for reading and displaying output data received from said computing unit.

30. A device according to claim 29, wherein the base unit has a memory for storing the measurement data and a connection for the transmission of the stored measurement data to an electronic data processing system.

31. A device according to claim 29, wherein a stationary testing device is included which is outfitted with a temperature sensor.

32. A device according to claim 29, wherein at least a number of testing devices have a probe head in which an additional measurement probe is installed.

33. A device according to claim 29, wherein a testing device has a plate-shaped probe head which is square as seen from the top.

34. A device according to claim 29, wherein a testing device has a cube-shaped probe head.

35. A device according to claim 29, wherein a testing device has a star-shaped probe head.

36. A device according to claim 29, wherein a testing device has an annular or cylindrical probe head.

37. A device according to claim 29, wherein at least one rotatable testing device has a probe head and a rigid, long connection member, and wherein a drive is included, having a motor, which is arranged in the base unit, and wherein the rigid connection piece is constructed for a detachable connection with the drive.

38. A device according to claim 37, wherein the rotatable testing device has a supporting rod which can be connected to the drive and has two probe heads at its end which are supported by a cross-piece so as to be arranged diametrically opposite one another.

39. A device according to claim 29, wherein at least one testing device has a probe head and a handle portion, at least one electronic circuit or control being installed in the handle portion for converting measured values occurring during operation of the probe head for transmission to the computing unit, which probe head is connected with the handle portion via a long, rigid or flexible connection member.

40. A device according to claim 39, in which the probe head is connected with the handle portion via a rigid connection member, wherein the connection member is connected with a drive which is arranged in the handle portion and serves to generate a rotating movement and/or a vibrating reciprocating movement of the connection member.

41. A device according to claim 40, wherein the connection member is constructed as a tube for the transmission of water under pressure, compressed air or a vacuum.

42. A method for on-site testing of unset concrete and mortar comprising the steps of:

provICES a portable, hand-held device having a base unit and a plurality of selectably attachable testing devices for generating measurement data of different parameters, at least one of said devices being constructed so as to be rotatable, said base unit having at least one connection for a testing device, said device having an energy source for operating the device independently of a main electrical supply, a computing unit, selector means for selecting a test to be carried out and thereby computing processes to be carried out by said computing unit, and a display for reading and displaying output data received from said computing unit;

inserting one of said testing devices into a different portion of a batch of unset concrete to provide measurement data; selecting a test to be carried out with respect to said measured data and related computer processes by said computing unit; and displaying output data of said computing unit.

43. The method of claim 42, including the steps of repeatedly inserting said testing device into said different portions of said batch of unset concrete to provide measurement data representing and averaging said measured data.

44. The method of claim 43, wherein said test to be carried is based on stored characteristic lines of standardized concrete recipes.

45. The method of claim 44, wherein said computing processes include a determination of at least one of a) slump, b) water/cement ratio and c) compressive strength.

* * * * *